United States Patent [19]
Hugens, Jr.

[11] Patent Number: 5,850,034
[45] Date of Patent: Dec. 15, 1998

[54] MAKING OF METAL PRODUCTS USING A GAS ANALYZER

[75] Inventor: John R. Hugens, Jr., Salt Lake City, Utah

[73] Assignee: ASARCO Incorporated, New York, N.Y.

[21] Appl. No.: 876,954

[22] Filed: Jun. 17, 1997

[51] Int. Cl.⁶ .............................. G01N 7/10; B22D 11/16
[52] U.S. Cl. .................. 73/19.07; 75/648; 75/384; 436/75; 436/144
[58] Field of Search ................ 73/19.01, 19.07, 73/19.1, 19.12; 75/384, 648; 148/508; 436/75, 134, 144, 145

[56] References Cited

U.S. PATENT DOCUMENTS

| | | | |
|---|---|---|---|
| 2,861,450 | 8/1958 | Ransley . | |
| 3,199,977 | 8/1965 | Phillips et al. | 75/649 |
| 3,926,623 | 12/1975 | Keyser et al. | 75/10.17 |
| 4,290,823 | 9/1981 | Dompas | 148/508 |
| 4,757,707 | 7/1988 | Harvey et al. | 73/19.07 |
| 4,907,440 | 3/1990 | Martin et al. | 73/19.07 |
| 5,037,471 | 8/1991 | Iwamura et al. | 75/648 |
| 5,293,924 | 3/1994 | Hugens, Jr. et al. | 164/452 |
| 5,518,931 | 5/1996 | Plessers | 73/19.07 X |

FOREIGN PATENT DOCUMENTS

| 140665 | 5/1990 | Japan | 73/19.07 |
|---|---|---|---|

OTHER PUBLICATIONS

"Extractive Metallurgy of Copper" by A.K. Biswas and W.G. Davenport, First Edition, Chapter 17, pp. 336–338, (no date).

"Continuous Casting and Rolling of Copper Rod at the M.H. Olen Copper Refinery Uses No Wheel" by J.M.A. Dompas, J.G. Smets, J.R. Schoofs; Wire Journal Sep. 1974, pp. 118–132.

"A/Scan In–Line Measurement of Hydrogen in Molten Aluminum" by Bomen Inc. (no date).

*Primary Examiner*—Daniel S. Larkin
*Attorney, Agent, or Firm*—DeLio & Peterson, LLC; John J. Tomaszewski; Kenneth A. Koch

[57] ABSTRACT

A method for improving the making of metals such as steel and copper by specially using a gas measurement system to analyze molten metals for gas, particularly H2 content, and to controlling the metal making process based on these values. The preferred gas analyzer comprises a hollow probe and an analyzer wherein the probe is immersed in the molten metal and a carrier gas containing a reducing gas such as CO is cycled through the probe and analyzer. The carrier gas entrains gases in the probe and this gas mixture is electronically compared with a reference value to provide a measurement of the gases in the molten metal and the process is controlled based on the analyzer results. Another important use of the gas analyzer is in molten metal degassing operations such as used in the steel

18 Claims, 3 Drawing Sheets

MAKING OF METAL PRODUCTS USING A GAS ANALYZER

BACKGROUND OF THE INVENTION

1. Field of the Invention

This invention relates to the making of a wide variety of metal products by processes such as extraction of the metal from the ore, purification processes, and mechanical working processes such as continuous casting and, more particularly, to improving the manufacturing method and the quality of the metal product, and in particular copper, by controlling process steps using a gas measurement system to measure the gas in the molten metal. The system comprises using an analyzer instrument and a probe wherein the probe is inserted into the molten metal at any of a number of process steps in the metal product making process and the use of a special carrier gas cycled in a circuit between the analyzer and the probe, the analyzer electronically comparing a reference value with the value obtained by a mixture of the carrier gas and gases entrapped in the probe to provide a gas measurement reading for the molten metal.

2. Description of Related Art

The manufacture of metals such as steel involves a number of processing steps from extraction of iron from the ore to the actual steel making step wherein molten iron is treated with oxygen and carbon to form the steel. In the steel making process and likewise in the copper making or other metal making process, molten metals are processed and eventually formed into the final product.

The manufacture of copper by continuous casting is well-known in the art. In the "Extractive Metallurgy of Copper" by A. K. Biswas and W. G. Davenport, First edition, Chapter 17, pages 336–368 the manufacturing process is described in detail and the disclosure is hereby incorporated by reference.

Basically, as described in Phillips et al., U.S. Pat. No. 3,199,977, which patent is hereby incorporated by reference, cathodes or other forms of pure copper are melted in a furnace and the molten copper fed to a holding furnace for casting. The Asarco shaft furnace is predominately employed and the copper is placed in the furnace at the top and is heated and melted as it descends down the shaft. The heat is provided by impinging and ascending combustion gases produced in burners near the bottom of the furnace. The following description will be directed to copper and this type furnace for convenience although it will be appreciated that other metals and other furnaces such as electric furnaces (no burners) may also be employed to provide molten metal which is then further processed into a metal final form.

The furnace is primarily a melting unit and the burners and combustion gases are such that the copper is generally not oxidized during melting. This is achieved by using specially designed burners which insure that unconsumed oxygen in the burner does not enter the furnace shaft and by controlling the fuel/air ratio of the burners to provide a slightly reducing atmosphere in the furnace. In generally, the fuel/air ratio is controlled to provide a reducing flame having a hydrogen content of the combusted fuel of up to about 3% by volume, usually 1%–3%.

There is generally no holding capacity in the furnace bottom and the molten copper flows immediately into a separate burner fired holding furnace. In many installations the launder connecting the shaft furnace and the holding furnace is also burner fired to likewise maintain the temperature of the copper and to minimize unwanted oxidation of the copper.

Copper containing oxygen is the predominant product in the market today and for convenience the following description will be directed to this product although it will be understood to those skilled in the art that the method may be used for other copper products (e.g., oxygen free-less than 20 ppm oxygen) and other metals such as steel. One form is tough pitch copper which is characterized by a level surface (flat set) after open-mold casting. The copper contains up to about 500 ppm oxygen or higher, preferably, 100–450 ppm, and is present in the form of copper oxide which is soluble in the molten copper and which forms copper oxide grains in the solid copper. Generally, the oxygen level is controlled by bubbling air through the molten copper in the holding furnace. Another method uses a burner in the holding furnace or launder having an oxidizing flame or reducing flame if necessary.

The molten copper from the holding furnace is then fed to a continuous caster such as a Properzi or Southwire wheel caster or a Hazelett twin belt caster. In the Hazelett caster, molten copper is cast between two coincidentally moving steel belts and the casting, usually a bar shape, is fed directly into a rod-rolling mill. The rod is normally discharged into a pickling unit, coiled and stored.

U.S. Pat. No. 4,290,823 granted to J. Dompas shows the basic continuous casting process for manufacturing copper and this patent is hereby incorporated by reference. The Dompas process produces an oxygen containing rod product which purportedly has the advantages of oxygen free copper (ductility) and the annealing capacity of tough pitch copper. The process uses a solid electrolyte containing an electrochemical cell to analyze the oxygen content of the molten copper in the holding furnace and adjusts the fuel/air ratio of the holding zone burners to maintain the desired oxygen level.

An article entitled "Continuous Casting and Rolling of Copper Rod at the M.H. Olen Copper Refiner Uses No Wheel", by J. M. A. Dompas, J. G. Smets and J. R. Schoofs (Wire Journal, September 1979, pages 118–132) also shows a typical rod making process.

Regardless of the particular processes and controls used, the main concern is to enhance the quality of the final copper product and meet standards relating to appearance (surface quality), electrical conductivity and physical behavior during fabrication and use.

Poor surface quality is generally indicative of a defective casting and industry employs a variety of tests to monitor this problem. The reason for a defective casting may be any of known and unknown reasons and one of the important tests uses an eddy-current defectometer (Defectomat Instrument) which records surface defects on the basis of severity. The surface quality detector may be employed at any position in the rod line after the metal is cast (e.g., after the caster and before the rolls, etc.) and is usually employed before the coiler and there is considered to be a direct correlation between the number of recorded defects and product quality. In general, constant checking of the recordings from the surface quality detector shows that the number of defects increases during the process because of roll wear and other mechanical problems and the detector enables the operator to determine when maintenance and adjustment of the rolls should be performed.

While various automatic mechanical type control techniques such as the surface quality detector are used in continuous casting systems, these techniques provide a relatively simple system for monitoring surface quality and do not control the more significant variables within the process directly or indirectly.

The same problems are encountered in making a wide variety of metals including steel and it is important to control operating parameters to provide a quality metal product. For example, hydrogen enbrittlement is a serious concern in steel manufacture and hydrogen control is very important in the steel making process. Degassing operations are an important process step in metal making and a reliable and efficient gas analyzer is essential for this purpose. Degassing may be performed using a wide variety of processes such as vacuum degassing, sparging the molten metal with an inert gas such as nitrogen or reacting the molten metal with a material that removes the unwanted gas such as $H_2$.

Bearing in mind the problems and deficiencies of the prior art, it is an object of the present invention to provide a method and apparatus for measuring the gas content of molten metals, particularly hydrogen, which measurements may be used to control or monitor the various steps of a metal making process.

It is a further object of the present invention to provide a novel system for the control of a continuous metal casting process.

Another object is to provide an improved method for the manufacture of metals such as copper and especially copper containing oxygen products, e.g., rod, tube, sheet and other forms by continuous casting.

A further object of the invention is to the use of the gas analyzer of the invention in molten metal degassing operations.

An additional object of the invention is to provide a gas analyzer for measuring the gas content of molten metals.

Other objects and advantages of the present invention will become apparent from the following detailed description.

SUMMARY OF THE INVENTION

It has now been discovered that the method for making metals, and in particular steel and copper, from the step of separation of the metal from the ore or other sources to the final product made by the steps of continuous casting or other means, may be improved by specially using a gas measurement system comprising an analyzer instrument and a probe wherein the probe, preferably hollow, is inserted into the molten metal and a reducing carrier gas, preferably carbon monoxide, is cycled in a circuit between the probe and the analyzer unit and a comparative reading obtained between a particular reference value and the value obtained by a mixture of the reducing carrier gas and gases in the probe which are entrained in the carrier gas. Gases in the probe are present in the molten metal and/or formed in the probe or at the probe interface. The gas reading is used to control parameters of the metal making process such as the fuel/air ratio of the burners employed in the melting furnace, launders, and/or holding furnace, in degassing operations and any other metal making step where analyzing of the gas content of the molten metal may be employed. The system is specially used by employing a reducing gas, e.g., carbon monoxide, as the carrier gas either partly, substantially, or wholly and/or by using a probe which contains carbon which reacts to form entrained CO when inserted into the molten metal. The system readings have been found to correlate with the surface quality of the cast product for copper making.

A preferred gas measurement system is sold by Bomem Inc. under the name ALSCAN and its operation and use are fully described in U.S. Pat. No. 4,907,440, which patent is hereby incorporated by reference. The instrument consists of two units, the analyzer and the probe, and was developed to measure the hydrogen content of liquid aluminum and related alloys Other suitable probes and analyzers may be used such as that used in the "Telegas" process described in U.S. Pat. No. 2,861,450 granted to Ransley et al. which patent is hereby incorporated by reference. This probe is open at the bottom (such as an inverted bell) with the carrier gas being fed into the open area of the probe and being removed at the top thereof. For convenience, the following description will be directed to use of the ALSCAN instrument although other similar type instruments may be used as will be appreciated by those skilled in the art.

Likewise, for convenience, the following description will be directed to the casting of copper although other molten metal systems in particular steel, may suitably be tested using the measurement system of the invention. Broadly stated, the method for making copper by continuous casting using a gas measurement system comprising an analyzer and a probe comprises:

(a) melting copper in a furnace;

(b) transferring the melted copper to a holding zone which is preferably heated;

(c) inserting into the molten copper a probe body, preferably hollow and preferably comprising a gas-permeable, liquid-metal-impervious material of sufficient heat resistance to withstand immersion in the molten copper, said probe having a gas inlet to its interior and a gas outlet therefrom the gas inlet and gas outlet being spaced from one another so that a reducing carrier gas passing from the inlet to the outlet traverses a substantial portion of the probe body interior for entrainment of gas formed therein or at the probe interface and/or diffusing to the interior of the body from the molten metal, the reducing carrier gas containing, partly or preferably wholly, a reducing gas such as CO which is used as the carrier gas or formed therein by using, for example, a carbon containing probe which reacts to form CO;

(d) comparing with an analyzer instrument by, e.g., electronic measuring means, the entrained gas and carrier gas mixture with a reference value, e.g., measuring the difference in resistivity of the entrained gas and carrier gas mixture and the reference value;

(e) adjusting, if necessary, the fuel/air ratio of one or more of the burners, the oxygen content of the molten copper or other operating parameters based on the analyzer results; and (f) repeating steps (c)–(e) during the casting operation.

In another aspect of the invention the probe may be inserted into a molten metal, such as steel, and using a reducing carrier gas such as CO, the gas content, predominately $H_2$, may be determined and this value used to control the degassing operation.

BRIEF DESCRIPTION OF THE DRAWINGS

The features of the invention believed to be novel and the elements characteristic of the invention are set forth with particularity in the appended claims. The figures are for illustration purposes only and are not drawn to scale the invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
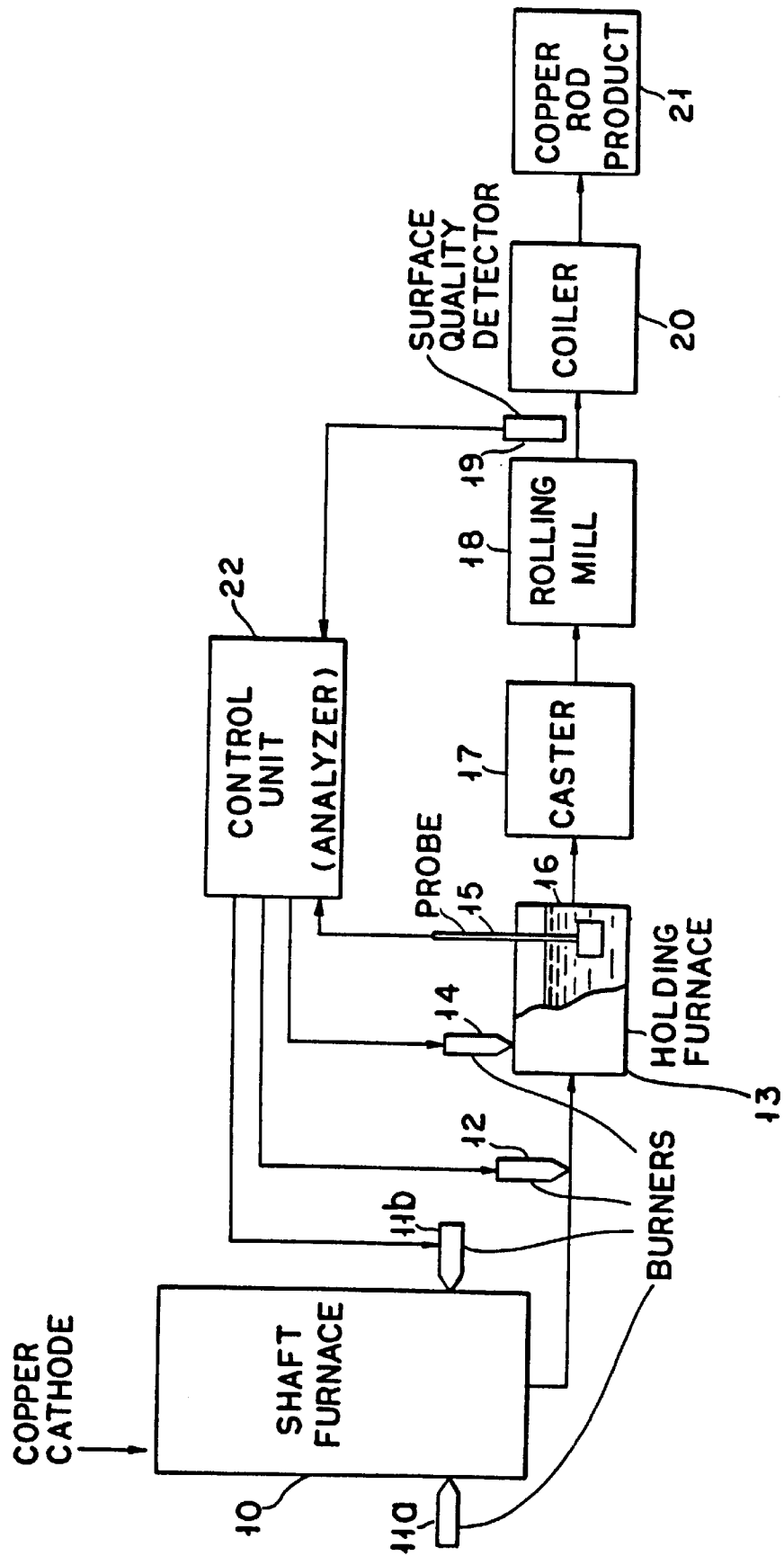
FIG. 1 shows a typical process flow chart of a copper rod continuous casting manufacturing process including as a portion thereof the use of the present invention.

In describing the preferred embodiment of the present invention, reference will be made herein to FIGS. 1–2 of the drawings in which like numerals refer to like features of the invention.

In general, the ALSCAN instrument relates the difference in electronic measurements between a reference value and a carrier gas-entrained gas mixture to the concentration of the gases in the molten metal and this value is outputted as an analyzer reading. As described in U.S. Pat. No. 4,907,440, the analyzer when used in molten aluminum measures the difference in resistivity of a bridge circuit which correlates this difference to the amount of hydrogen in the molten aluminum (see FIG. 2). As discussed in the patent, the difference in resistivity of the resistance wires is caused by, in effect, a difference in thermal conductivity of the entrained and carrier gas mixture and the reference gas. When hydrogen is present in the aluminum, the carrier gas (nitrogen)-entrained gas mixture thus contains hydrogen and the thermal conductivity is higher than the carrier gas alone and causes increased cooling of the wire, which difference is electronically measured and correlated. As described in the patent, the comparison cell of the analyzer (catharometer) is open to the atmosphere since air is a suitable reference gas in the aluminum system when the carrier gas is nitrogen. The instrument may also be operated without a comparison cell by using a reference value instead of a reference gas, the reference value being the same value as if a reference gas were employed in the comparison cell.

When the instrument is used in a copper system, however, the resulting curve when using nitrogen as the carrier gas does not resemble the curve for an aluminum bath, which is the subject of U.S. Pat. No. 5,293,924 assigned to the assignee of this invention. Referring to FIG. 2, it can clearly be seen that use of nitrogen as the carrier gas with the carbon containing probe 15 of FIG. 1 in an aluminum system to measure hydrogen is completely different from its use in the more complex copper metallurgical system where oxygen and hydrogen are both in solution but not necessarily in equilibrium with each other especially during the continuous casting process where the variable are constantly changing. Other gases and copper oxide generated in the process are also present in the melt. Thus, as shown in FIG. 2 and in U.S. Pat. No. 4,907,440, the analyzer readings reach a peak and that peak is maintained (in equilibrium) during immersion of the probe and operation of the instrument in the molten aluminum. The peak is correlated to measure the hydrogen level of the melt in the aluminum system.

In the copper system however, which contains a number of other gases, particularly oxygen, it is hypothesized that an initial peak is usually obtained which probably represents hydrogen, but that the readings often fall to a lower equilibrium value (point A) because gases in the copper system combine either in the probe or at the melt-probe interface to produce a different gas mixture than existing in the melt, said mixture having different thermal conductivities from the individual gases present in the melt. Depending on the probe design, flow of metal around the probe, operation of the instrument, etc., a peak may not be obtained but rather readings which reach an equilibrium value. Modification of the ALSCAN gas analyzer system however, using a reducing gas in the carrier gas will provide a similar behavior for measuring the gas content of metals as the use of nitrogen does in an aluminum system. This is shown by curves B and C of FIG. 2 which will be further discussed hereinbelow.

Referring now to FIG. 1, a typical copper continuous casting process in conjunction with using the probe (analyzer) and method of the invention is shown. Copper cathodes or other copper forms are added to the shaft furnace 10 and melted using burners 11a and 11b. Molten copper flows from the furnace into holding furnace 13. The molten copper may be heated during transfer from the shaft furnace 10 to holding furnace 13 by burner 12 and in the holding furnace by burner 14. Probe 15 is inserted into the molten copper 16 and the entrained gas mixture from the probe is relayed to control unit 22. The probe may also be inserted, for example, into the launder connecting the shaft furnace 10 to the holding furnace 16, the launder connecting the holding furnace 16 to the caster 17 or in the tundish of the caster 17. A separate analyzer instrument may be used to electronically compare the gases entrained in the probe with the results inputted to control unit 22. In FIG. 1, the control unit 22 also contains the analyzer instrument as an integral part thereof and which measures and compares the entrained gas-carrier gas mixture in the probe with a reference value and provides an analyzer reading to be used by the control unit. The molten copper 16 is fed into caster 17 and the casting fed into rolling mill 18 to produce the copper rod product 21. Coiler 20 is normally employed to coil the copper for storage. A surface quality detector 19 is used to measure the surface quality of the rod with the output being relayed to control unit 22. Based on the signals relayed to the control unit 22 by detector 19 and probe (analyzer) 15, control signals are relayed to the burners to adjust, if necessary, the fuel/air ratios.

Control signals may also be used to adjust other process variables to control the process, for example, oxygen levels, adjusting of particular burners in the system, exposing the copper to other reducing or oxidizing agents, purging of the copper with neutral substances (nitrogen), temperature level, agitation of the melt to remove gases, etc. In one embodiment, control of the oxygen level based on the analyzer results may be accomplished using an oxygen probe which measures the amount of oxygen in the molten copper In a typical run, the oxygen level of the copper will be controlled at a level of about 100–450 ppm, preferably 140–400 ppm and most preferably 240–280 ppm by introduction of air into or over the surface of the copper.

In operation, the probe 15 will be inserted into the molten copper 16 and signals from the analyzer will be sent to control unit 22 based on the gases in the molten metal.

Basically, the preferred probe 15 consists of a monolithic body of a gas-permeable, liquid-metal-impervious material having a desired porosity and pore size. The porosity is defined as the proportion of the total value of the body that is occupied by the voids within the body and a suitable range is about 5% to about 80% or higher. The pore size can vary over a wide range usually about 0.5 micrometers to 2,000 micrometers or higher. Generally, tubes extend into the probe body 15, one tube for introducing the carrier gas and another tube for transferring the carrier gas and, after immersion in the molten copper, entrained gases from the molten metal (and any gases formed which are within the probe body) are cycled to an analyzer which electronically measures and compares the carrier gas and the entrained gases mixture with a reference value. The analyzer computes an output which is used by the control unit 22 to control the process. It will be understood that the term entrained gases include gases which are formed within the probe or at the probe-molten metal interface by individual gases existing in the molten metal combining (e.g., chemical reaction) due to the temperature, proximity of the gases in the probe, probe-melt interface reaction, etc. It is an important feature of the invention that a reducing gas such as carbon monoxide be present in the carrier gas or be used wholly as the carrier gas. This can be accomplished by using CO as the carrier gas completely or as a mixture with another carrier gas such as nitrogen or argon. For a mixture, amounts of reducing gas, e.g., CO, of about 1 to 99% by volume preferably greater than 10% and most preferably greater than 50 or 75% may be used. Another method employs a carbon containing probe which under the conditions present in the copper making process reacts to form CO which is entrained in the carrier gas. This method is not preferred however, as shown by point A of FIG. 2 wherein the time to equilibrium is relatively long (e.g., 600 seconds).

Figure 3:
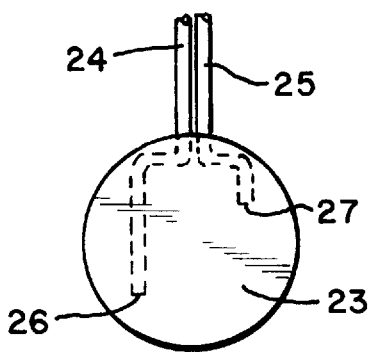
FIGS. 3–8 are elevation views of different configurations of probe members used in the invention.
Figure 4:
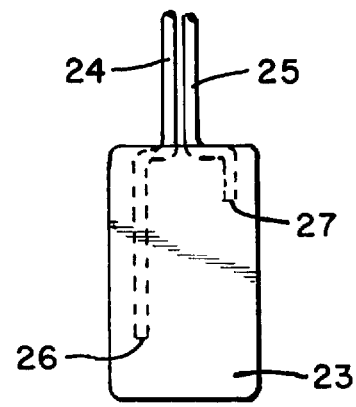
Figure 5:
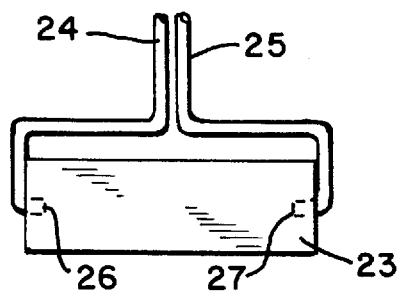
Figure 6:
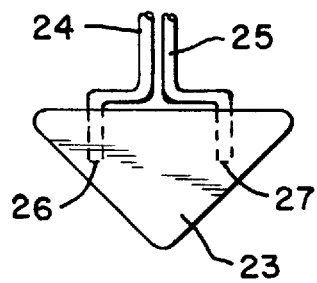
Figure 7:
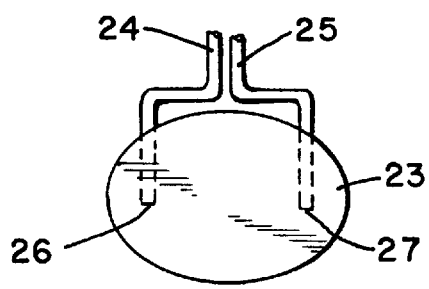
Figure 8:
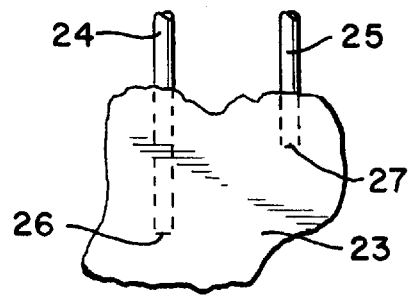

The probes of the invention can take a number of different forms, and some examples are shown in FIGS. 3–8. FIG. 3 is a complete circular disk, the tubes 24 and 25 extending different distances into the body 23 to increase the length of the flow path between the inlet 26 and outlet 27. FIG. 4 shows a rectangular body that is somewhat longer than it is wide, with tubes 24 and 25 extending different distances into the body, as with the structure of FIG. 3, while FIG. 5 shows a probe with a cylindrical body, the tubes 24 and 25 entering at opposite ends. FIG. 6 Illustrates a triangular-shaped probe body and FIG. 7 an elliptical-shaped body, while FIG. 8 shows that a quite irregular-shaped body that a suitable material can be provided with a gas inlet and outlet and function successfully.

In a typical preferred copper rod manufacturing operation, the probe 15 typically a carbon material will be flushed with CO as the carrier gas (and the thermal conductivity of CO used to establish the reference value) for a length of time to ensure that only CO remains in the circuit. The flushing is then stopped and the probe 15 immersed into the molten copper 16 with the volume of carrier gas in the circuit being constantly circulated through the probe and the analyzer electrical measuring means. Upon immersion, gases in the molten copper 16 enter the porous probe body 15 or are formed therein and the circulation of the carrier gas and entrained gas mixture is continued until substantial equilibrium is reached-about 1 minute (point C of FIG. 2). At the end of this period or continually over a time period as shown in FIG. 2, the analyzer takes a measurement of the electronic comparative difference between the reference value and entrained gases and carrier gas mixture and converts this difference into an analyzer reading.

Figure 2:
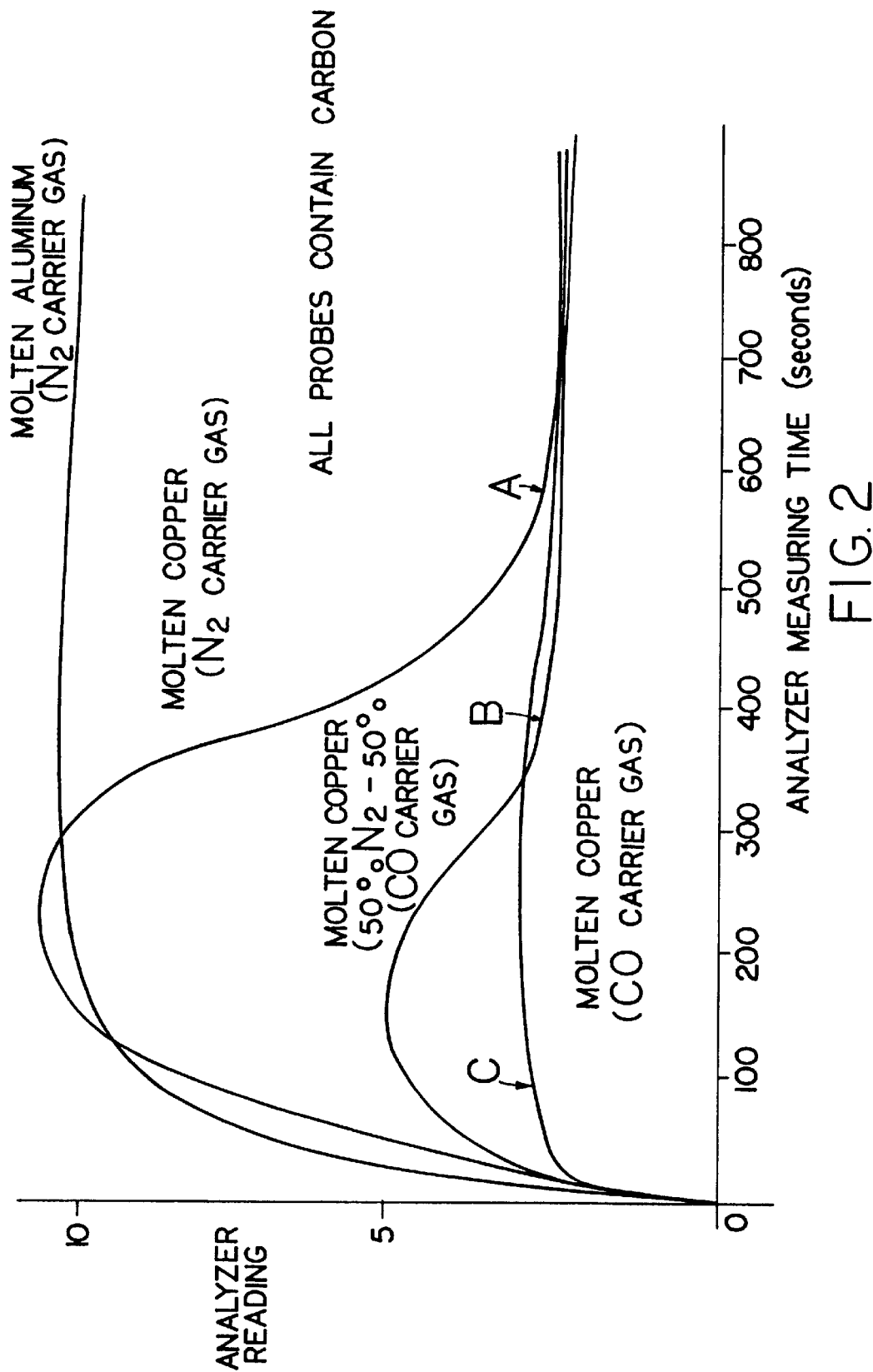
FIG. 2 is a graph comparing typical analyzer instrument readings versus time when the gas measurement system is used to measure molten copper and molten aluminum using different carrier gases.

While the instrument may be normalized or correlated to produce readings based on any scale, FIG. 2 shows that when the probe and analyzer are used as detailed in U.S. Pat. No. 4,907,440, with the exception that the carrier gas is CO, the readings rise and reach a plateau indicating equilibrium. As shown in FIG. 2, equilibrium is reached substantially faster when CO is the carrier gas. Compare points A, B, and C. This equilibrium will be affected by the probe properties (pore size, etc.) and has been found using a commercial instrument (ALSCAN Instrument (HMA0100D) made by Bomem Inc.) to be established after immersion for about 1 minute, where CO is the total carrier gas, and the readings obtained will remain fairly constant after this time barring upsets in the rod manufacturing process or changes in the operating parameters. It is hypothesized that the reducing gas, e.g., CO, reacts with the gases present in the molten copper to provide an entrained gas-carrier gas mixture which reaches equilibrium quickly and which is an accurate measurement for controlling the copper making process. One reducing reaction is probably the conversion of water in the copper to $H_2$ and $CO_2$. Other similar reducing reactions are also probably occurring simultaneously with the equilibrium mixture, again, being an accurate measurement for controlling the process.

It is an important feature of the invention that the analyzer readings be used to control the process using the control unit 22 since the readings have been found to correlate with the surface quality of the rod.

In a typical operations, the probe 15 is activated and readings obtained. If the readings after equilibrium are at the desired set point no changes are made to the process. If the readings increase, the fuel/air ratios will be decreased to achieve the desired reading. Thus, if the $O_2$ content of the copper increases, the fuel/air ratios of the shaft furnace burners are normally increased. Oxygen levels will normally not be changed and will continue to be monitored and maintained at desired operating levels. Operation of a commercial shaft furnace and caster and rolling mill using this procedure resulted in a controlled process with the rod having fewer surface defects that when operated without the gas analysis probe.

In other metal making operations such as a degassing operation in a steel making process, the probe is inserted into the molten steel (metal) using CO or other reducing gas as the carrier gas in the gas analyzer system. A reading will be obtained which can be correlated to the hydrogen and other gas content of the molten steel and the degassing operations controlled based on this value. Vacuum, sparging or chemical reaction may be used to control the process based on the gas value as described above.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for making metal by measuring the gas content of a molten metal using a gas measurement system comprising an analyzer and a probe the method comprising the steps of:

melting the metal;

inserting into the molten metal a probe body comprising a gas-permeable, liquid-metal impervious material of sufficient heat resistance to withstand immersion in the molten metal, said probe having a gas inlet to its interior and a gas outlet therefrom, the gas inlet and gas outlet being spaced from one another so that a carrier gas containing a reducing gas passing from the inlet to the outlet traverses a substantial portion of the probe body interior for entrainment of gas in the probe body which gas diffuses into the probe body from the molten metal;

comparing with an analyzer instrument the entrained gas and carrier gas mixture with a reference value using electronic measuring means; and determining the gas content of the molten metal and controlling the metal making process based on the gas content value.

2. The method of claim 1 wherein the reducing gas is CO.

3. The method of claim 2 wherein the carrier gas is substantially CO.

4. The method of claim 2 wherein the CO in the carrier gas is provided by using a carbon containing probe.

5. The method of claim 1 wherein the metal is copper.

6. The method of claim 5 wherein the molten copper is copper being fed to a continuous caster to make a copper rod.

7. The method of claim 1 wherein the metal is steel.

8. The method of claim 7 wherein the molten steel is measured for gas content during a degassing operation.

9. The method of claim 8 wherein the gas being measured is hydrogen.

10. A method for making copper by continuous casting using a gas measurement system comprising an analyzer and a probe comprising:

melting copper in a furnace;

transferring the molten copper to a heated holding zone;

inserting into the molten copper a probe body comprising a gas-permeable, liquid-metal impervious material of sufficient heat resistance to withstand immersion in the molten copper, said probe having a gas inlet to its interior and a gas outlet therefrom, the gas inlet and gas outlet being spaced from one another so that a carrier gas containing a reducing gas passing from the inlet to the outlet traverses a substantial portion of the probe body interior for entrainment of gas in the probe body which gas diffuses into the probe body from the molten metal;

comparing with an analyzer instrument the entrained gas and carrier gas mixture with a reference value using electronic measuring means;

determining the gas content of the copper;

adjusting, if necessary, one or more of the operating parameters based on the gas content; and repeating the above steps during the casting operation.

11. The method of claim 10 wherein the reducing gas is CO.

12. The method of claim 11 wherein the carrier gas is substantially CO.

13. The method of claim 11 wherein the CO in the carrier gas is provided by using a carbon containing probe.

14. A gas analyzer for measuring the gas content of molten metals comprising;

a probe body comprising a gas-permeable, liquid-metal impervious material of sufficient heat resistance to withstand immersion in the molten metal, said probe having a gas inlet to its interior and a gas outlet therefrom, the gas inlet and gas outlet being spaced from one another so that a carrier gas containing a reducing gas passing from the inlet to the outlet traverses a substantial portion of the probe body interior for entrainment of gas in the probe body which gas diffuses into the probe body from the molten metal; and an analyzer instrument for comparing the outlet entrained gas and carrier gas mixture with a reference value using electronic measuring means to determine the gas content of the molten metal.

15. The gas analyzer of claim 14 wherein the reducing gas is CO.

16. The gas analyzer of claim 15 wherein the carrier gas is substantially CO.

17. The gas analyzer of clam 15 wherein the CO in the carrier gas is provided by using a carbon containing probe.

18. The gas analyzer of claim 14 wherein the probe body is open at the bottom.

* * * * *